US005710086A

United States Patent [19]
Brunelle et al.

[11] Patent Number: 5,710,086
[45] Date of Patent: Jan. 20, 1998

[54] TITANATE CATALYSTS

[75] Inventors: Daniel Joseph Brunelle, Burnt Hills; Tohru Takekoshi, Scotia; Judith Ann Serth-Guzzo, Slingerlands, all of N.Y.

[73] Assignee: General Electric Company, Schenectady, N.Y.

[21] Appl. No.: 618,738

[22] Filed: Mar. 20, 1996

[51] Int. Cl.$^6$ .............................. B01J 31/00; C07F 7/00; C07F 7/28

[52] U.S. Cl. .......................... 502/171; 502/162; 556/21; 556/54; 556/56

[58] Field of Search .................... 556/21, 54, 56; 502/162, 171

[56] References Cited

U.S. PATENT DOCUMENTS

| | | | |
|---|---|---|---|
| 2,643,262 | 6/1953 | Bostwick | 556/54 |
| 3,091,625 | 5/1963 | Gilsdorf | 556/54 |
| 3,119,852 | 1/1964 | Gilsdorf | 556/54 |
| 3,320,193 | 5/1967 | Beck et al. | 556/56 |
| 3,892,791 | 7/1975 | Brook et al. | 556/56 |
| 4,438,039 | 3/1984 | Beers et al. | 556/175 |

FOREIGN PATENT DOCUMENTS

| | | | |
|---|---|---|---|
| 776694 | 1/1968 | Canada | 556/54 |
| 2012925 | 9/1970 | Germany | 556/56 |
| 41-12909 | 7/1966 | Japan | 556/54 |
| 57-200471 | 12/1982 | Japan | 556/56 |

*Primary Examiner*—Glenn Caldarola
*Assistant Examiner*—J. Pasterczyk
*Attorney, Agent, or Firm*—William H. Pittman

[57] ABSTRACT

Reaction mixtures prepared from tetraalkyl titanates and mixtures of glycols, said reaction mixtures comprising titanium bisglycoxide oligomers, may be used as depolymerization catalysts for conversion of linear polyesters to macrocyclic polyester oligomers.

5 Claims, No Drawings

TITANATE CATALYSTS

This invention was made with Government support under Contract No. N70NANB2H1237 awarded by the US Government. The Government has certain rights in this invention.

FIELD OF THE INVENTION

This invention relates to novel catalysts which may be employed for making macrocyclic polyester oligomers. More particularly, the invention is directed to titanate catalysts that are substantially free of monofunctional alcohols and monofunctional titanium alkoxides and they unexpectedly do not interfere with the stability of desired macrocyclic polyester oligomers when employed as depolymerization catalysts.

BACKGROUND OF THE INVENTION

Linear polyesters such as poly(alkylene terephthalates) are well known commercially available polymers. They have many valuable characteristics including strength, toughness, high gloss and solvent resistance. Linear polyesters are conventionally prepared by the reaction of a diol with a functional derivative of a dicarboxylic acid, typically a diacid halide or ester. Further, the above-described polyesters may be fabricated into articles by a number of well known techniques including injection and roto molding and extrusion.

In recent years, macrocyclic polyester oligomers have been developed and desired since they have unique properties which make them attractive as matrices for polymer composites. Such desired properties stem from the fact that macrocyclic polyester oligomers exhibit low viscosities, allowing them to impregnate a dense fibrous preform easily. Furthermore, such macrocyclic polyester oligomers melt and polymerize at temperatures well below the melting point of the resulting polymer. Thus, melt flow, polymerization and crystallization can occur isothermally and, therefore, the time and expense required to thermally cycle a tool is favorably reduced.

Previously known methods for producing macrocyclic polyester oligomers typically employ amine catalysts and corrosive acid halides such as terephthaloyl chloride. Such methods are often undesirable since they require environmentally unfriendly halides and expensive recycling steps associated with the formation of byproduct amine salts.

Still additional methods employ the use of dialkyl tin catalysts which often result in environmentally unfriendly byproducts and also oligomers that are not thermally stable.

The instant invention, therefore, is directed to novel catalysts which may be employed for producing macrocyclic polyester oligomers, and the catalysts are not environmentally unfriendly.

DESCRIPTION OF THE PRIOR ART

Processes for preparing polyesters have been disclosed in the art. In commonly assigned U.S. Pat. No. 5,039,783, macrocyclic polyester oligomers are prepared via the condensation of diols with diacid chlorides in the presence of non-sterically hindered amine catalysts.

Additionally, in commonly assigned U.S. Pat. No. 4,132,707, a method for converting linear polyesters to branched copolyesters is described. In said method, poly(alkylene terephthalate) is combined with a mixture of phenol and tetrachloroethane and a branching component in order to produce a solid particulate blend. The solid particulate blend is subsequently heated in the presence of an inert gas in order to produce the desired branched copolyester.

Finally, in commonly assigned U.S. Pat. No. 5,407,984, a method is disclosed for producing linear polyesters from macrocyclic polyester oligomers with a tin containing catalyst.

SUMMARY OF THE INVENTION

In a first aspect, the instant invention is directed to novel reaction products, said reaction products are selected from the group consisting of:

(a) the mixture of reaction products of

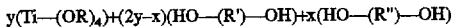
$$y(Ti—(OR)_4)+(2y-x)(HO—(R')—OH)+x(HO—(R'')—OH)$$

wherein said reaction product is substantially free of monofunctional alcohols and monofunctional titanium alkoxides and each R is independently a $C_1$–$C_{10}$ alkyl group, each R' is independently a $C_2$ to $C_6$ alkylene group, R'' is a $C_2$ to $C_{12}$ substituted alkytene, x is the number of moles of glycols present and has a value of greater than or equal to 0, and y is the number of moles of Ti present and has the value of greater than 0; and (b) the mixture of reaction products of

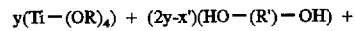
$$y(Ti—(OR)_4) + (2y-x')(HO—(R')—OH) +$$

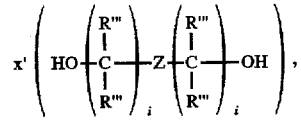

wherein said reaction product is substantially free of monofunctional alcohols and monofunctional titanium alkoxides and each R, R', R'' and y are as previously defined, each R''' is independently a hydrogen or $C_1$ to $C_4$ alkyl group, x' is the number of moles of glycols present and has the value of greater than 0, and Z is sulfur, phosphorus groups, nitrogen groups or preferably oxygen and each i is independently an integer from 2 to 4. The phosphorus groups often have the formula

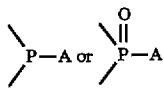

wherein A is hydrogen or a $C_1$–$C_8$ alkyl group or an aryl group. The nitrogen groups are often

wherein A is as previously defined.

Moreover, the mixture of reaction products may be prepared in the presence or absence of organic solvents, and they may be isolated from any monofunctional alcohols and monofunctional titanium alkoxides made in the process. Additionally, the mixture of reaction products described above may be employed to depolymerize linear polyesters, producing stable macrocyclic polyester oligomers. Stable macrocyclic polyester oligomers are defined to mean oligomers that do not undergo premature polymerizations without the addition of a polymerization catalyst.

DETAILED DESCRIPTION OF THE PREFERRED EMBODIMENTS

Regarding the reagents used to prepare the mixture of reaction products described in (a) and (b), each R is preferably an isopropyl or butyl group, R' is preferably an ethylene or butylene group, R" is preferably a hydrocarbon substituted $C_3$ propylene, and R'" is preferably hydrogen. Such reagents are commercially available and often made by conventional methods. The titanium alkoxides, for example, are typically made by reacting an alcohol with titanium tetrachloride. The glycols, for example, may be prepared by the hydrolysis of epoxides, hydroxylations with osmium tetroxide and the Reppe process. Other methods are disclosed in *Industrial Organic Chemistry*, Second Edition, Revised and Extended Edition, (1993), the disclosure of which is incorporated herein by reference.

The mixture of reaction products themselves are prepared via metathesis reactions. The methathesis reactions are not limited to any apparatus or processing steps. Often, however, they are conducted in a reaction vessel having a means for stirring/agitation, heating and distilling/refluxing. Typically, the reagents are added to such a reaction vessel, no particular order being required. Stirring/agitation and/or heating may be employed to enhance product formation. Often, the reaction temperature is from about ambient to about 140° C. An organic solvent is often employed for enhancement of the reaction (although the reaction may proceed in the absence of solvents) and an inert gas purge may also be employed to prevent hydrolysis and oxidation of reagents as well as other undesirable ancillary side reactions. The organic solvents are essentially not limited and often include o-xylene, chlorobenzene, naphthalene, toluene, tetramethylbenzene, methylnaphthalene, o-dichlorobenzene, or mixtures thereof. Preferably, no proton donating compounds like water or acids are present during the reaction. The desired mixture of reaction products, which may be used as a depolymerization catalyst, may be used as is in solution. Additionally the products may be recovered by first precipitating the mixture of reaction products from solution by cooling or adding an anti-solvent, followed by filtration.

Additionally, the mixture of the reaction products obtained often comprises butanediol bis-(triethanolaminatotitanate) (IV), bis[{2,2'-(methylimino)bis [ethanolato]}(2)-N,O,O']titanium III, titanium bisbutyleneglycoxide or mixtures thereof.

Substantially free of monofunctional alcohols and monofunctional alkoxides is defined herein to mean that the reaction product is at least about 90% and preferably at least about 95% free of all monofunctional alcohols and monofunctional alkoxides, determined by the absence of alkoxide groups originally present. The removal of the monofunctional alcohols and monofunctional alkoxides may be enhanced, for example, via vacuum or pressure reduction in the reaction vessel. Typically, the monofunctional alkoxides are converted to monofunctional alcohols in the reaction and they are removed as such via vacuum, pressure reduction or distillation.

Depolymerization is defined herein to mean the conversion of linear polyesters to macrocyclic polyester oligomers having a molecular weight of less than said polyester linear. The reaction products described above may be employed to depolymerize linear polyesters; therefore, such reaction products may be described as depolymerization catalysts. The linear polyesters which may be depolymerized are often poly(alkylene dicarboxylates) and typically of the family consisting of polymeric glycol terephthalates or isophthalates and mixtures thereof including copolyesters of terephthalic and isophthalic acids. Especially preferred linear polyesters depolymerized by the mixture of the reaction products described in this invention include poly(1,2-ethylene terephthalate) (PET) and poly(1,4-butylene terephthalate) (PBT) and copolyesters comprising the same. Said copolyesters typically comprise less than about 25% by weight PET but preferably less than about 15% by weight PET. Other preferred linear polyesters include poly(1,2-ethylene 2,6-naphthalenedicarboxylate) (PEN) and the like. A more detailed description of the production of macrocyclic polyester oligomers via the depolymerization of linear polyesters is described in commonly assigned U.S. application Ser. No. 08/618,742, now U.S. Pat. No. 5,668,186, the disclosure of which is incorporated herein by reference.

Additionally, it is noted herein that the mixtures of reaction products described above when employed as polyester depolymerization catalysts unexpectedly do not interfere with the stability of the desired macrocyclic polyesters produced. For example, alkyl tin catalysts when used as depolymerization catalysts for polyesters invariably become incorporated into the macrocyclic polyester oligomers produced. This, in turn, causes the oligomers to undergo premature polymerizations upon heating, rendering them unstable and difficult to work with. The mixtures of reaction products described above when used as polyester polymerization catalysts are not incorporated into the resulting oligomers. They, therefore, do not cause premature polymerization of the oligomers produced in their presence.

Moreover, it is noted herein that in most cases the mixture of reaction products defined above unexpectedly display at least one of the improved properties selected from the group consisting of greater hydrolytic stability when compared to conventional depolymerization catalysts and enhanced solubilities in organic solvents. Also, when the reaction products are employed in polyester depolymerizations, the resulting macrocyclic polyester oligomers unexpectedly are not contaminated with monofunctional ester capped linear oligomers.

The following examples further illustrate and facilitate the understanding of the instant invention. The products obtained may be confirmed by conventional techniques such as proton and carbon 13 nuclear magnetic resonance spectroscopy and GPC analysis.

EXAMPLE 1

A 250 mL three neck flask equipped with a distillation adapter was charged with 27.8 grams (0.31 moles) of 1,4-butanediol, 10.194 grams (0.077 moles) of 2,2-diethyl-1,3-propanediol, 54.8 grams (0.193 moles) of tetraisopropyl titanate and 70 mL of dry (nitrogen purged) o-xylene. The resulting mixture was stirred and heated under nitrogen. Isopropanol was produced and distilled off over a period of 50 minutes during which time the resulting reaction solution was at a temperature of about 140° C. The solution was clear and viscous and was diluted with an additional 20 mL of dry o-xylene. The resulting diluted solution was cooled producing a mixture of reaction products comprising titanium bisglycoxide in a clear homogeneous solution (118 grams of product mixture comprising 39.2wt % titanium bisglycoxide, 1.63 meq/g of Ti).

EXAMPLE 2

A 250 mL flask equipped with a distillation adapter, was charged with 9.01 grams (0.10 moles) of 1,4-butanediol, 10.612 grams(0.10 moles) diethylene glycol (bis-2-hydroxyethylether) 28.43 grams (0.10 moles) of tetraisopropyl titanate. The resulting mixture was stirred and heated under nitrogen. Isopropanol was produced and distilled off over a period of 50 minutes during which time the resulting reaction solution rose to a temperature of about 140° C. Subsequently, 150 mL of o-xylene were added resulting in a clear solution. Proton NMR analysis of the resulting solution indicated that no isoproxy groups were present. The clear resulting solution was diluted to 200 mL by adding additional dry o-xylene. Upon cooling, the resulting mixture of reaction products was a gum-like titanium bisglycoxide comprising mixture.

EXAMPLE 3

Example 3 was conducted in a manner similar to the one described in example 2 except that 75.0 mmol of butanediol, 25.0 mmol of diethylene glycol and 50.0 mmol of tetraisopropyl titanate were reacted and the solvent employed was a 1:1 mixture of o-xylene and o-dichlorobenzene in lieu of straight o-xylene. The resulting mixture of reaction products was a titanium bisglycoxide comprising solution.

EXAMPLE 4

A 1L resin kettle was charged with 108.83 grams (1.21 moles) 1,4-butanediol 1.71.63 grams (0.60 moles) of tetraisopropyl titanate 200 mL of dry (nitrogen purged) toluene. The resulting mixture was stirred under nitrogen and heated to distill off any isopropanol produced. During approximately 2 hours of distillation, 200 mL of toluene were added in about 50 mL portions. The resulting solution was heated to about 110° C. and a viscous polymeric phase separated on the bottom of the kettle. The distillation was continued for an additional half hour and a total of 225 grams of distillate (isopropanol and toluene) were collected resulting in a gum-like product in the kettle. The kettle was transferred to a dry box where the resulting supernatant toluene phase was poured off. The gummy product which remained was pulled out of the kettle with a tweezer and placed into a jar for drying under vacuum. The resulting brittle solid was ground into a white powder and redried under vacuum. The mixture of resulting reaction products contained about 136.8 grams of titanium bisbutyleneglycoxide.

EXAMPLE 5

A reaction vessel equipped with a stirrer and heating means was charged with 7.10 grams (25.0 mmol) titanium (IV) isopropoxide, 5.96 grams (50.0 mmol) N-methyldiethanolamine and 50 mL of dry (nitrogen purged) o-xylene. The resulting mixture was heated under nitrogen and after reaching about 100° C., isopropanol began to distill off. The resulting solution's temperature rose to about 160° C. and o-xylene began to distill off. The volume of the solution was adjusted to produce a 1.0M solution in o-xylene. Proton NMR showed that no isopropyl groups remained in the resulting mixture of resulting reaction products which contained bis[{2,2'-(methylimino)bis [ethanolato]}(2)-N,O,O']titanium IV.

EXAMPLE 6

A reaction vessel equipped with a stirrer and heating means was charged with 12.66 grams (50.0 mmol) of titanium (IV) (triethanolaminato) isopropoxide, 2.25 grams (25 mmol)1,4-butanediol and 100 mL of dry (nitrogen purged) o-xylene to produce a mixture. The mixture was stirred and heated to about 100° C. after which isopropanol began to distill off. Distillation continued until the resulting solution reached 160° C. and o-xylene began to distill off. The volume of the solution was adjusted to produce a 0.5M solution in o-xylene. Proton NMR showed that no isopropyl groups remained in the resulting mixture of resulting reaction products which contained butanediol bis-(triethanolaminatotitanate) (IV).

EXAMPLE 7

Example 7 was conducted in a manner similar to the one described in Example 2 except that 50.0 mmol of butanediol, 50.0 mmol of diethylene glycol and 50.0 mmol of tetraisopropyl titanate were reacted and the solvent employed was a 1:1 mixture of o-xylene and o-dichlorobenzene in lieu of straight o-xylene. The resulting mixture of reaction products was a titanium bisglycoxide comprising solution.

What is claimed is:

1. A mixture of reaction products of $$y(Ti-(OR)_4) + (2y-x')(HO-(R')-OH) +$$

$$x'\left(HO \begin{pmatrix} R''' \\ | \\ -C- \\ | \\ R''' \end{pmatrix}_i -Z- \begin{pmatrix} R''' \\ | \\ -C- \\ | \\ R''' \end{pmatrix}_i OH\right),$$

said mixture being substantially free of monofunctional alcohols and titanium alkoxides corresponding thereto; wherein each R is independently $C_1$–$C_{10}$ alkyl, each R' is independently $C_2$–$C_6$ alkylene, each R''' is independently hydrogen or $C_1$–$C_4$ alkyl, Z is oxygen, sulfur, a nitrogen-containing group or a phosphorus-containing group, each of x' and y has a value greater than 0, and each i is independently an integer from 2 to 4.

2. A mixture according to claim 1 wherein each R is isopropyl or butyl, R' is ethylene or butylene and R''' is hydrogen.

3. A mixture according to claim 1 wherein Z has the formula $$\begin{array}{c} \diagdown \\ P-A, \\ \diagup \end{array} \quad \begin{array}{c} \diagdown \overset{O}{\underset{\|}{}} \\ P-A \text{ or} \\ \diagup \end{array} \quad \begin{array}{c} \diagdown \\ N-A, \\ \diagup \end{array}$$

wherein A is hydrogen, $C_1$–$C_4$ alkyl or aryl.

4. A mixture according to claim 1 wherein R' is 1,4-butylene, each R''' is hydrogen, Z is oxygen and i is 2.

5. A composition comprising at least one of $$Ti\begin{bmatrix} O-(CH_2)_2 \\ \diagdown \\ N-CH_3 \\ \diagup \\ O-(CH_2)_2 \end{bmatrix}_2 \quad \text{and}$$

$$N\begin{matrix} (CH_2)_2-O \\ (CH_2)_2-O \\ (CH_2)_2-O \end{matrix} Ti-O-(CH_2)_4-O-Ti \begin{matrix} O-(CH_2)_2 \\ O-(CH_2)_2 \\ O-(CH_2)_2 \end{matrix} N.$$

* * * * *